United States Patent
Eaton et al.

[11] Patent Number: 5,871,504
[45] Date of Patent: Feb. 16, 1999

[54] ANCHOR ASSEMBLY AND METHOD FOR SECURING LIGAMENTS TO BONE

[76] Inventors: Katulle Koco Eaton, 4766 Royal Palm Cir., N.E., St. Petersburg, Fla. 33703; Joseph Fucci, 2346 Grove Valley Ave., Palm Harbor, Fla. 34683; Steven E. Fitts, 5295 Olivet Dr., Ridge Manor, Fla. 33523; Sharon K. Anderson, 9563 Sun Isle Dr., N.E., St. Petersburg, Fla. 33702

[21] Appl. No.: 954,781

[22] Filed: Oct. 21, 1997

[51] Int. Cl.⁶ ..................................................... A61F 5/04
[52] U.S. Cl. ............................................. 606/232; 606/73
[58] Field of Search ..................................... 606/232, 233, 606/65, 66, 72, 86–89, 73, 90, 99, 74, 76; 623/13, 16, 20; 604/164–167

[56] References Cited

U.S. PATENT DOCUMENTS

| | | |
|---|---|---|
| Re. 34,293 | 6/1993 | Goble et al. . |
| 3,953,896 | 5/1976 | Treace . |
| 4,409,974 | 10/1983 | Freedland . |
| 4,590,928 | 5/1986 | Hunt et al. . |
| 4,708,132 | 11/1987 | Silvestrini . |
| 4,716,893 | 1/1988 | Fischer et al. . |
| 4,744,793 | 5/1988 | Parr et al. . |
| 4,772,286 | 9/1988 | Goble et al. . |
| 4,784,126 | 11/1988 | Hourahane . |
| 4,870,957 | 10/1989 | Goble et al. ................. 606/232jf124c |

FOREIGN PATENT DOCUMENTS

| | | |
|---|---|---|
| 9639105 | 12/1996 | WIPO . |
| 9730649 | 8/1997 | WIPO . |

OTHER PUBLICATIONS

"The Paramax ACL Guide System Surgical Technique," brochure, Linvatec Corporation, 1992.
"Endoscopic Technique for ACL Reconstruction with Pro-Trac Tibial Guide: Endobutton Fixation" (undated).

*Primary Examiner*—Michael Buiz
*Assistant Examiner*—Vikki Trinh
*Attorney, Agent, or Firm*—Michael de Angeli

[57] ABSTRACT

Improved ligament anchor structures and methods for affixing graft ligaments to bone are provided. The ligament anchor assembly includes a sleeve having gripping means for being firmly secured within a bone tunnel and a bore extending therethrough. The graft ligament is secured to an insert sized to pass through the bore in the sleeve. The bore in the sleeve and the external surface of the insert have cooperating asymmetrical teeth formed thereon so that the insert can pass through the sleeve in only one direction. The sleeve is first placed in a bone tunnel and the opposite end of the ligament secured in the corresponding bone, followed by final adjustment of the ligament tension without disturbing the anchors of either end of the graft ligament.

40 Claims, 3 Drawing Sheets

U.S. PATENT DOCUMENTS

| | | | |
|---|---|---|---|
| 4,927,421 | 5/1990 | Goble et al. . | |
| 4,950,270 | 8/1990 | Bowman et al. | 606/72 |
| 4,955,910 | 9/1990 | Bolesky | 623/13 |
| 5,139,520 | 8/1992 | Rosenberg . | |
| 5,147,362 | 9/1992 | Goble . | |
| 5,152,790 | 10/1992 | Rosenberg et al. . | |
| 5,234,435 | 8/1993 | Seagrave, Jr. . | |
| 5,246,425 | 9/1993 | Hunsberger et al. | 604/165 |
| 5,257,996 | 11/1993 | Mc Guire . | |
| 5,268,001 | 12/1993 | Nicholson et al. . | |
| 5,269,809 | 12/1993 | Hayhurst et al. . | |
| 5,306,301 | 4/1994 | Graf et al. . | |
| 5,312,438 | 5/1994 | Johnson . | |
| 5,350,399 | 9/1994 | Erlebacher et al. . | |
| 5,354,298 | 10/1994 | Lee et al. . | |
| 5,356,413 | 10/1994 | Martins et al. . | |
| 5,356,435 | 10/1994 | Thein . | |
| 5,370,662 | 12/1994 | Stone et al. | 606/232 |
| 5,372,599 | 12/1994 | Martins . | |
| 5,423,819 | 6/1995 | Small et al. . | |
| 5,423,858 | 6/1995 | Bolanos et al. . | |
| 5,425,767 | 6/1995 | Steininger et al. . | |
| 5,456,685 | 10/1995 | Huebner | 606/73 |
| 5,456,721 | 10/1995 | Legrand . | |
| 5,464,427 | 11/1995 | Curtis et al. . | |
| 5,466,243 | 11/1995 | Schmieding et al. | 606/232 |
| 5,507,754 | 4/1996 | Green et al. . | |
| 5,549,619 | 8/1996 | Peters et al. . | |
| 5,562,668 | 10/1996 | Johnson . | |
| 5,562,671 | 10/1996 | Goble et al. . | |
| 5,570,706 | 11/1996 | Howell . | |
| 5,571,104 | 11/1996 | Li . | |
| 5,571,139 | 11/1996 | Jenkins, Jr. . | |
| 5,584,835 | 12/1996 | Greenfield . | |
| 5,603,716 | 2/1997 | Morgan et al. . | |
| 5,632,748 | 5/1997 | Beck, Jr. et al. . | |
| 5,643,266 | 7/1997 | Li . | |
| 5,645,547 | 7/1997 | Coleman . | |
| 5,649,940 | 7/1997 | Hart et al. . | |

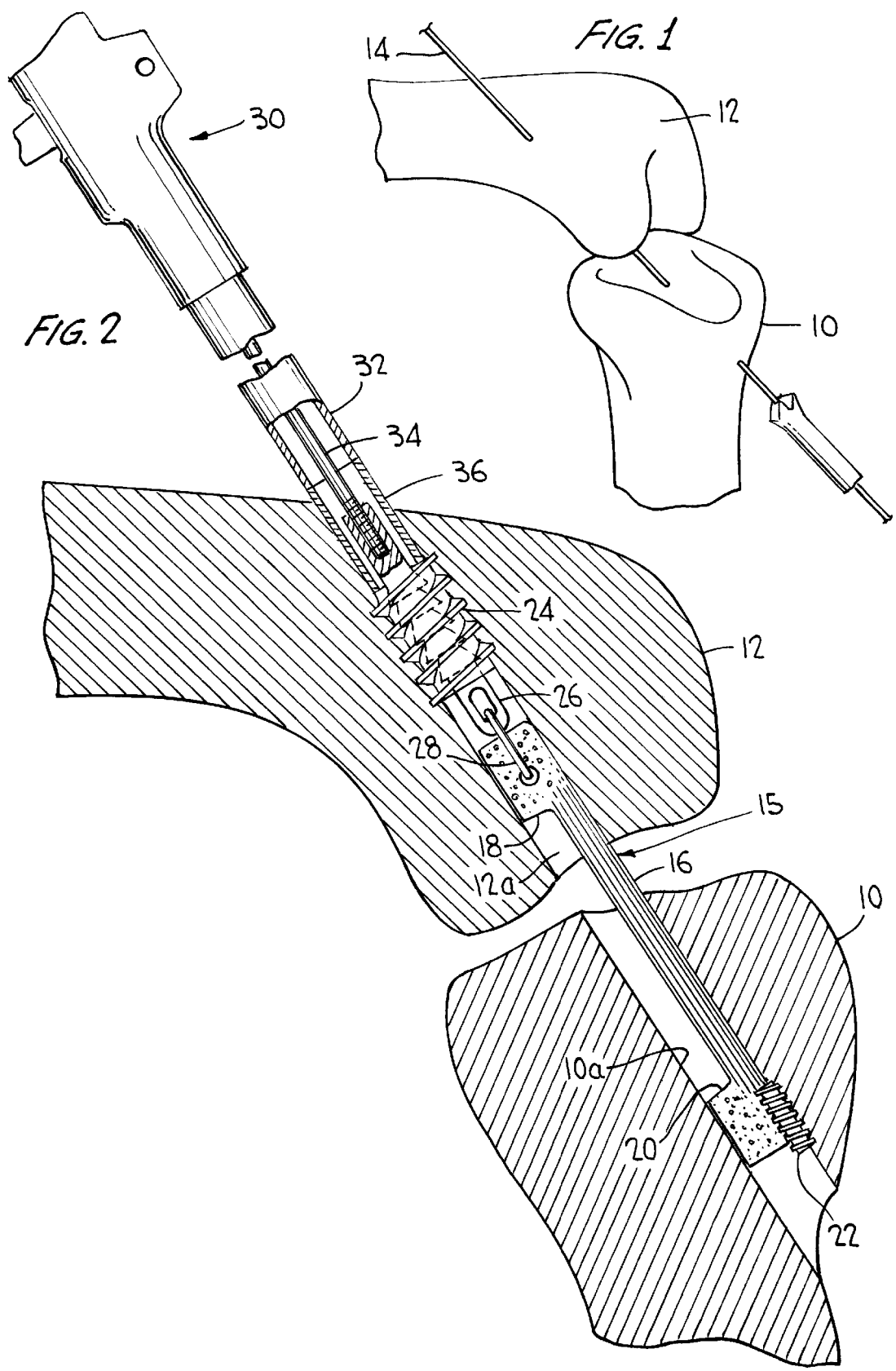

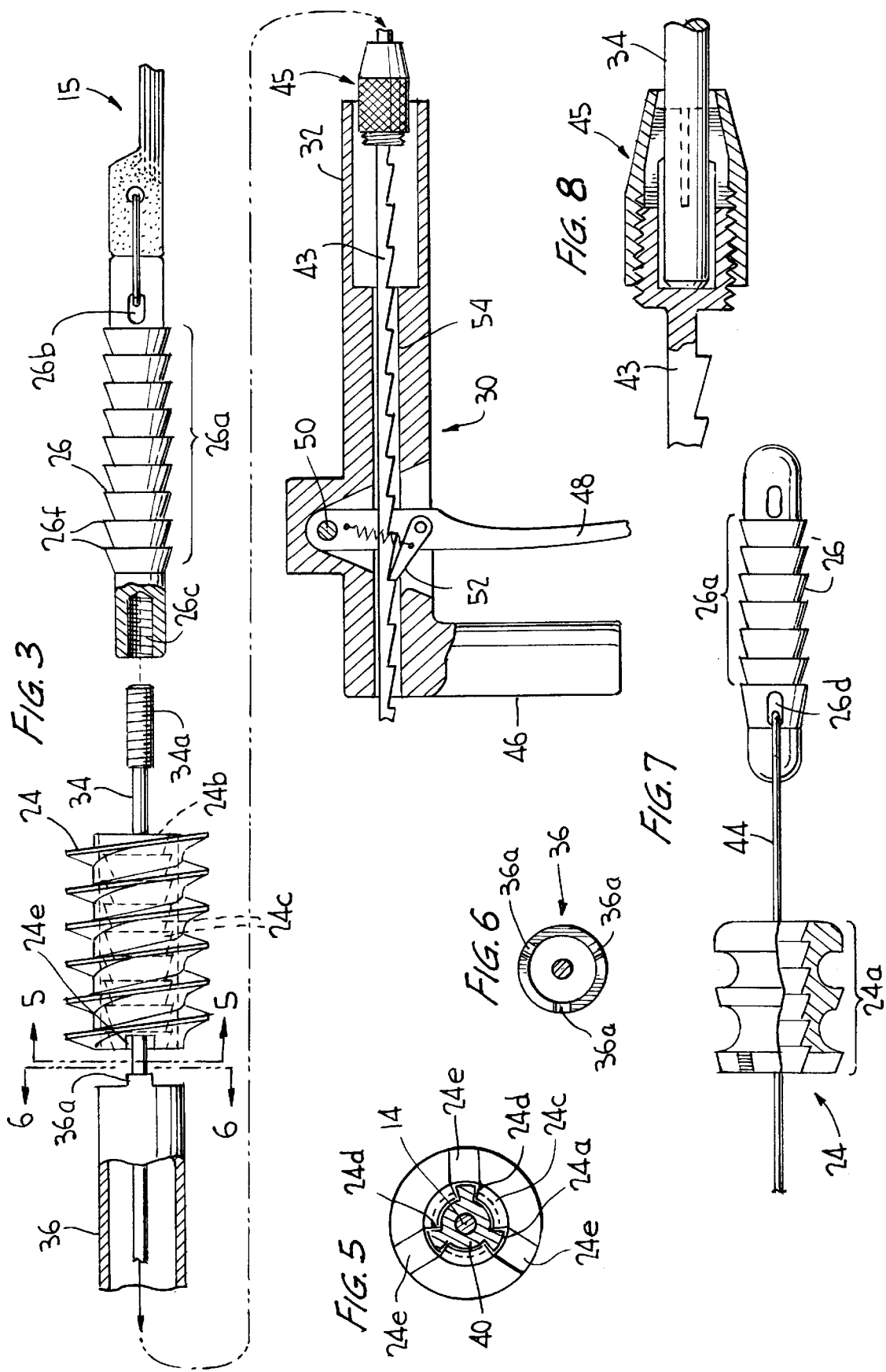

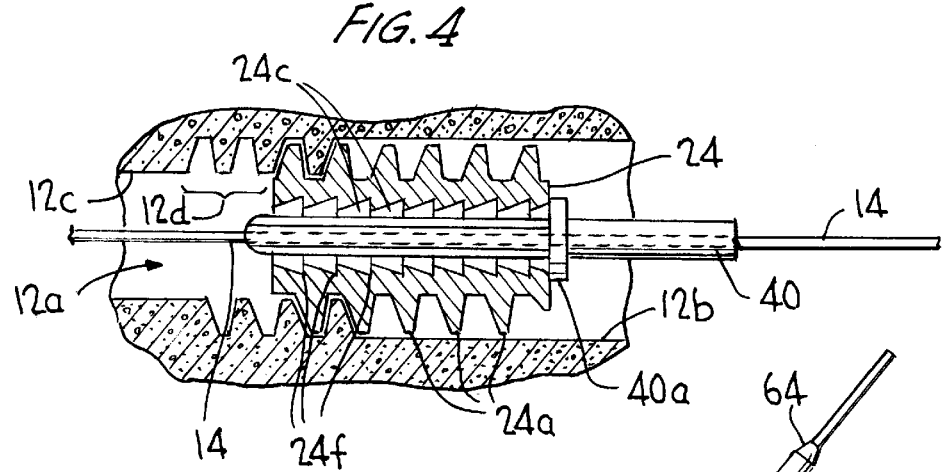
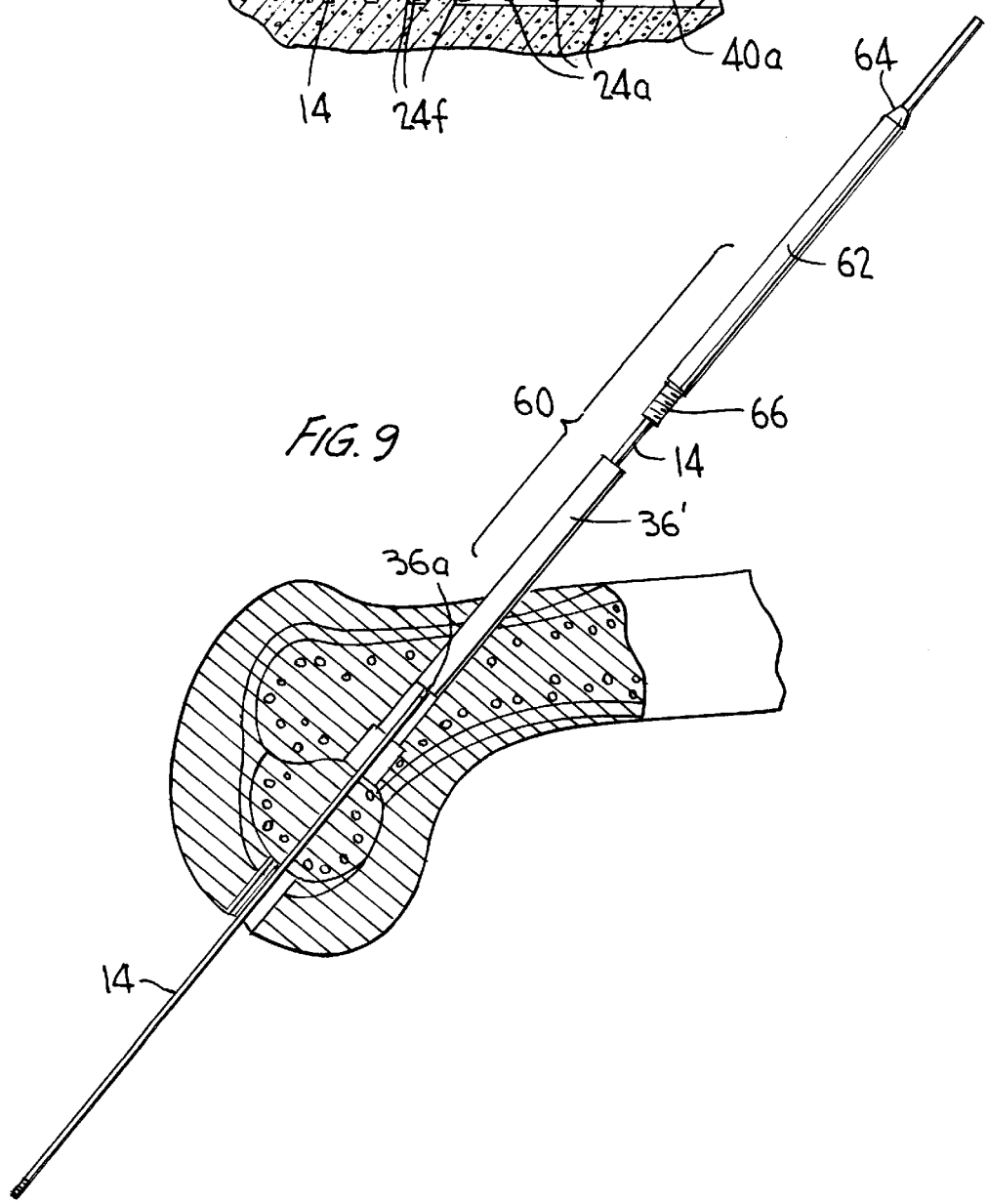

ANCHOR ASSEMBLY AND METHOD FOR SECURING LIGAMENTS TO BONE

FIELD OF THE INVENTION

This invention relates to an improved anchor assembly and method for joining ligaments to bone, in particular, as used for anterior cruciate ligament reconstruction.

BACKGROUND OF THE INVENTION

Due to the frequency of injury to the anterior cruciate ligament (ACL), especially in sports, and similar injury to other ligaments and related structures, there is a great deal of prior art dealing with replacement of these structures with graft ligaments. Much of this prior art is concerned principally with ensuring proper alignment of bone tunnels drilled in the tibia and femur to receive the opposed ends of the graft ligament, preparation of the surgical site, i.e., by removing sufficient bone to allow the graft to function properly, and with preparation of suitable graft ligaments, commonly by harvesting donor bone/tendon/bone structures from the knee of the patient. See generally, "The Paramax ACL Guide System Surgical Technique", a brochure published by Linvatec Corporation of Largo, Florida in 1992, and incorporated by reference herein. Other sources of replacement ligaments, including allograft and autograft ligament substitutes, are within the skill of the art and are intended to be included within "graft ligament" as used herein.

The present invention does not address these aspects of ACL reconstruction, but instead addresses the problem of securely anchoring the graft ligament in the bone tunnels while properly tensioning the ligament so as to provide support for the joint.

The prior art also addresses the concerns of properly anchoring and tensioning the graft ligament. However, the prior art known to the inventor does not provide a fully satisfactory anchor mechanism whereby both ends of the graft can be anchored in opposed tunnels in the tibia and femur, followed by final adjustment of the ligament tension. That is, preferably the anchors (or other attachment means employed) at both ends of the graft ligament would first be secured in their ultimate positions, followed by final adjustment of the ligament tension, in order to provide proper joint articulation. To the limited extent the prior art provides this capability (see the discussion of Johnson U.S. Pat. No. 5,562,668 below), the anchor structures known are undesirably complex, bulky, and hard to use properly.

More specifically, a common prior art ACL replacement practice is described in U.S. Pat. No. 5,306,301 to Graf. A flat planar ligament anchor is first attached to the femur end of the graft ligament, and is passed upwardly from below, so as to pass entirely through bone tunnels formed in the tibia and in the femur; after the planar anchor exits the proximal end of the bore, it is turned so as to bear against the outer surface of the femur. The opposite end of the graft is then fixed to the tibia. No adjustment of the ligament tension is possible after the ends of the ligament graft are fixed.

This technique requires that the overall length of the assembly be determined accurately before the graft is fabricated and secured to the tibia and femur. A difference in the ligament length of as little as a few millimeters is critical in provision of correct joint articulation. However, measurements of this accuracy are very difficult to determine in advance, as there are many variables involved, including the relative depth to which the anchors will be inserted into the bone tunnels, and the working length of the graft ligament, which in turn will vary depending on the degree of tightness with which the ligament graft is sutured to the anchor(s), the degree of stretch in the ligament itself, and so forth. It would be far more satisfactory if the surgeon could simply fabricate the graft ligament to an approximate overall dimension, anchor both ends in their final positions, and then make final tension adjustments. This ability would simplify the surgical procedure and yield better joint articulation after repair.

As indicated above, U.S. Pat. No. 5,562,668 to Johnson teaches a tensioning device for ligament grafts. At least one end of the graft is fixed to a carrier having a screw-threaded cylindrical member extending toward the outer surface of the joint. The carrier is received by a nut in turn received within a thimble. After the carrier is threaded into the nut, a process which would appear difficult in practice, the nut can be turned further, drawing the carrier further into the thimble. The nut can only be turned using a special tensioning key, which must be hollow in order to pass a wire needed to make the initial assembly of the carrier to the nut.

While the Johnson structure would permit adjustment of the tension on the ligament after seating of the thimbles in the bone tunnels, the degree of adjustment provided is constrained by the linear extent of the thread formed on the carrier, in turn requiring relatively exacting measurement of the overall distance between the anchoring points, and necessitating that the length of the ligament be controlled to correspond to this distance, complicating the procedure. The Johnson assembly also includes a relatively large number of parts, requires a special tool, requires a relatively large-diameter bore in the bone to receive the carrier and thimble, and takes up a significant fraction of the distance between the anchors, reducing the overall length of the ligament itself.

Rosenberg U.S. Pat. No. 5,152,790 shows a relatively complex three-component anchor assembly for ACL reconstruction. A first of Rosenberg's components includes a shank having threads formed on its outer surf ace for engaging the bone, and having a smooth internal bore. Torque is transmitted to the first component by a second component having a bore with a cross-section suitable for receiving torque from an associated driver. The second component is laser welded or otherwise bonded to the first component in order that a third component, to which the ligament is affixed, can rotate with respect to the first and second components. In this way, the ligament to be fixed by Rosenberg's device is not twisted as the first threaded component is drawn into a bore in a bone by torque exerted on the bore of the second component.

Rosenberg's anchor can thus be threaded into a bore in a bone, but there is no separate adjustment provided for the tension on the ligament. For example, if the ligament is fully tensioned before the threaded component is seated properly, the procedure must be repeated. Of course, the other end of the ligament could be affixed only after the anchor attached to the first had been seated, but this would not allow tension adjustment after anchor securing, as desired. Rosenberg's anchor is also excessively complex and bulky.

Other prior art generally relevant to this invention includes U.S. Pat. No. 4,870,957 to Goble, disclosing tubular threaded anchors for insertion into bone tunnels, followed by insertion of snap-fitting securing members from the inside of the joint. Not only would this insertion step be rather difficult to perform, the tension adjustment possible thereafter would be constrained by the degree to which the anchors could be moved in the bone tunnels without disturbing their secure seating.

U.S. Pat. No. 4,772,286 to Goble (now Reissue Pat. No. 34,293) also discloses several embodiments of methods and anchor structures for ACL replacement. The anchors shown in FIGS. 2–5 of Goble are expanding conical structures. It appears that although these anchors are threadedly attached to the ends of the ligament graft, their relative position cannot be adjusted after the anchors are secured in their final position; that is, the threaded members are provided simply to ensure secure fixation of the anchors, and do not allow for subsequent tension adjustment.

In a second embodiment, shown in several variations in FIGS. 6–11, Goble teaches attaching the graft to the femur by threading a screw fixed to one end of the graft into a tunnel drilled in the femur; the opposite end is secured in the tibia by turning a conical nut threaded over a fitting at the tibia end of the ligament against a seat formed in the tibia. This again requires the tension adjustment and tibial securing of the ligament end to be accomplished simultaneously; that is, the surgeon does not have independent control of the securing of the graft ligament in the tibia and of ligament tension.

U.S. Pat. No. 5,643,266 to Li also shows anchors for ACL replacement or similar procedures involving expanding anchors. In Li, the tension on the ligament must be adjusted before the anchors are secured in place. See col. 6, lines 11–24. Hence the ligament tension may vary as the anchors are expanded and secured.

Treace U.S. Pat. No. 3,953,896 shows a prosthetic ligament assembly including opposed conical threaded nut members for securing the ends of a prosthetic ligament in bone tunnels, and sleeves for protecting the ligament against abrasion. Treace mentions (col. 4, line 48) that the tension on the ligament is adjusted by turning the nut members; it appears that the fit of the nut members on the bone tunnels would substantially limit the degree of adjustment provided.

Other patents generally relevant to the subject matter of this application include Greenfield U.S. Pat. No. 5,584,835, showing a device for affixing tissue to bone. A threaded bone anchor is first threaded into the bone; the soft tissue is then sutured to a suture anchor. The outer surface of the suture anchor and a recess in the bone anchor are provided with cooperating asymmetrical teeth, so that the suture anchor can readily be inserted into but is securely retained by the bone anchor. No provision is made for adjustment of tension in a soft-tissue structure thus affixed to bone.

U.S. Pat. No. 5,350,399 to Erlebacher shows a structure for sealing puncture wounds in blood vessels and the like wherein an intra-arterial occluder and an extra-arterial occluder are drawn toward and secured to one another by a sawtooth-shaped guide extending from the intra-arterial occluder, through the wound, and over which the extra-arterial occluder is placed; when the two are drawn together, the sawteeth on the guide prevent them from slipping apart. A tool is provided for drawing the guide out through the extra-arterial occluder while holding the latter in position.

Patents showing anchors for securing ligament ends and other tissue structure to bone that do not provide subsequent adjustment of tension include Morgan U.S. Pat. No. 5,603,716; Beck U.S. Pat. No. 5,632,748; Thein U.S. Pat. No. 5,356,435; Steininger U.S. Pat. No. 5,425,767; Silvestrini U.S. Pat. No. 4,708,132; Parr U.S. Pat. No. 4,744,793; Coleman U.S. Pat. No. 5,645,547; Goble U.S. Pat. No. 4,927,421; and others.

OBJECTS OF THE INVENTION

It is therefore an object of the invention to provide a bone anchor for anchoring a ligament graft or similar structure to bone, whereby the tension in the structure can be adjusted after anchors at its ends are secured in their final position.

It is a further object of the invention to provide a bone anchor of the type described above which is simpler, involves fewer parts, and can be more easily employed than those of the prior art.

It is a further object of the invention to provide a method for anchoring an end of a ligament graft or similar structure in bone wherein the tension on the ligament or other structure can be adjusted after the anchor has been secured in its final desired position.

It is a further object of the invention to provide an improved method for replacement of ligaments and similar surgical procedures.

SUMMARY OF THE INVENTION

The objects of the invention mentioned above, and others which will become apparent as the discussion below proceeds, are met by the present invention, comprising a method and anchor apparatus for securing graft ligaments and similar structures to bone. The anchor assembly of the invention comprises a sleeve and an insert. The sleeve is generally tubular in shape and has gripping members formed on an outer surface thereof for being securely received within tunnels formed in the tibia and femur. For example, in ACL replacement, the sleeve will typically be secured within a bore in the femur. The insert is secured to the graft ligament. The outer surface of the insert and the surface of the bore in the sleeve comprise cooperating asymmetrical toothed structures, such that the insert can be pulled through the sleeve in one direction, but is precluded from motion therethrough in the opposite direction.

According to the method of the invention, the sleeve is affixed in a bone tunnel in a final desired position. Several different embodiments of the sleeve are provided, such that the sleeve may be threaded into a tapped bone tunnel or pushed into a smooth-walled bore. One end of the insert is assembled to the graft ligament and a tension member is attached to the opposite end of the insert. In typical ACL replacement, the sleeve is placed in a tunnel in the femur. The tension member is then inserted through an incision in the patient's lower leg, passes through a tunnel in the tibia, into the tunnel in the femur, through the sleeve, and out through the opposite end of the bone tunnel and a second incision in the thigh. The insert is then pulled through the bone tunnel in the tibia, into the bone tunnel in the femur, and up into the sleeve having previously been placed in the femur. The lower end of the ligament is then fixed to the tibia using a similar anchor assembly, or using known interference screws or like structures. At that point, the anchor is fixed in position in the femur, and the opposite end of the graft is fixed in the tibia. Thereafter, tension in the ligament can be adjusted simply by pulling the insert further into the sleeve; the cooperating tooth members provide a "ratcheting" one-way action or motion to the insert within the sleeve. A tool may be provided to exert tension on the insert for this purpose.

In a particularly preferred embodiment of the method of the invention, the tunnel through the femur is drilled using a hollow trocar or drill bit threadedly attached to a cannula. This assembly is threaded over a guide wire to ensure proper alignement of the tunnels. After the tunnel has been cut, the trocar (or drill, if used) is unscrewed from the cannula, leaving the cannula in place. The cannula can then be used to restrain motion of the sleeve as the insert is pulled through the sleeve, and can be used to remove or reposition the sleeve if necessary.

BRIEF DESCRIPTION OF THE DRAWINGS

The invention will be better understood if reference is made to the accompanying drawings, in which:

FIG. 1 shows an overall prospective schematic view of the femur and tibia showing the relationship thereof;

FIG. 2 shows a cross-sectional view through bone tunnels formed in the femur and tibia and shows the assembly of a graft ligament and ligament anchor structure according to the invention;

FIG. 3 shows an elevational view of essentially the same assembly, together with a tool used for exerting tension on the insert;

FIG. 4 shows a cross-sectional view of one embodiment of the insert;

FIGS. 5 and 6 are end views of the insert and a cannula which can be used to turn the sleeve in the bone tunnel;

FIG. 7 shows alternate embodiments of the sleeve and insert;

FIG. 8 shows a detail of FIG. 3; and

FIG. 9 shows a perspective view of a tool useful in practice of a particular embodiment of the method of the invention, illustrating the manner of its use.

DESCRIPTION OF THE PREFERRED EMBODIMENTS

FIG. 1 shows, as mentioned, an overall perspective view of the knee joint. Tibia 10 is juxtaposed to the femur 12 at the knee. A guide wire 14 is shown extending between the tibia and the femur. The anterior cruciate ligament (ACL) normally connects the opposed faces of the femur and tibia along the line indicated in FIG. 1 by guide wire 14. Replacement of the ACL, for example after damage due to lateral impact against the knee, is now a very common surgical procedure. The present invention, as mentioned above, is particularly directed at improvements in graft anchoring techniques used for ACL replacement, and to improvements in ACL replacement methods, but is not limited thereto; the anchor assembly and methods of the invention can be applied to repair and replacement of other ligamentary and similar structures within the body.

FIG. 2 shows a cross-sectional view taken through the femur 12 and tibia 10 illustrating bone tunnels 12a and 10a respectively; the bone tunnels are essentially holes drilled through the femur 12 and tibia 10 over guide wire 14. The placement of guide wire 14 and the formation of bone tunnels 10a and 12a, and in particular the alignment of the tunnels in the tibia and femur, can be performed as set forth in the "The Paramax ACL Guide System Surgical Technique" brochure mentioned above; the tunnels may also be formed using a novel combined trocar and cannula described in detail below.

As shown in FIG. 2, the goal of the technique is essentially to replace a damaged ACL with a graft ligament 15, in this example a bone-tendon-bone graft comprising a tendon bridge section 16 connected to two bone plugs 18 and 20. Typically such graft ligaments 15 are harvested from the patient's knee as described in the brochure referred to above, but securing of graft ligaments prepared in other ways well known to those of skill in the art is also within the scope of the invention.

In typical practice of the method of the present invention, the distal or tibial end of the ligament graft 15 can be fixed to the tibia using an interference screw 22 of known type, or other known techniques. The proximal or femoral end of the graft ligament 15 is secured using the inventive anchor structure, the anchor structure comprising a sleeve 24 fixed in the tunnel 12a in the femur 12 and shown in more detail in FIGS. 3 and 4, and an insert 26, also shown in more detail in FIG. 3, sutured to the ligament graft 15. The insert may be sutured directly to the graft, as shown, or may be spaced therefrom by on the order of 5 mm. Alternative embodiments of the sleeve and insert are shown in FIG. 7, discussed below.

As discussed in detail above, the prior art shows techniques and anchor assemblies for ACL replacement where both ends of the graft ligament structure can be fixed with respect to their respective bones, and in which the tension of the ligament can thereafter be adjusted by movement of the end of the ligament with respect to its respective anchor. See, e.g., the Johnson reference. However, the structures shown in this and other known prior art are undesirably complex, bulky, and cumbersome.

According to the present invention, a smaller, simplified anchor structure is provided, while providing the same advantage of adjustment of ligament tension after securing of the anchors in the bone.

In performance of ACL replacement according to the method of the present invention, the sleeve 24 is first secured in the bone tunnel 12a having been drilled in the femur. The sleeve 24 may be inserted and driven into place through the femoral tunnel from above, or through the antero-medial portal on the lower side of the femur. As shown in FIG. 4, the bone tunnel 12a preferably includes a distal section 12b large enough to pass the sleeve without interference, and a proximal section 12c of smaller diameter where the sleeve is to be placed; if desired, the proximal section 12c of the bone tunnel may be tapped as indicated at 12d to receive a threaded sleeve inserted from below.

The assembly of insert 26 with graft ligament 15 attached is then inserted through the distal end of the tunnel 10a in the tibia, and is pulled through the femoral tunnel 12a until the graft is in substantially its desired position. If a "stepped" tunnel having sections 12b, 12c of differing dimensions is used, the lengths of these sections of the tunnels may be chosen to accomodate the length of the graft being used. Insert 26 is pulled into sleeve 24 until the tibial end of the graft ligament 15 (that is, bone plug 20 of the bone-tendon-bone graft shown) is in its desired position within the tibial tunnel 10a. The tibial end of the graft ligament is then secured in position. The tension on the graft 15 is then adjusted as needed by varying the position of insert 26 with respect to sleeve 24, as explained further below, to provide proper joint articulation.

Preferably, insert 26 is pulled through sleeve 24 using a tool 30 shown schematically in FIG. 2 and also in FIG. 3. Tool 30 exerts tension on a tension rod 34 removably attached to the end of insert 26. When tool 30 is operated, rod 34 is pulled into a coaxial tubular member 32, pulling insert 26 into sleeve 24 and tensioning graft 15. Tubular member 32 bears directly or through an intermediate cannula 36 (FIG. 2) against the proximal end of sleeve 24, to hold the sleeve 24 in position while tension rod 34 exerts axial tension on insert 26, as shown. Guide wire 14 (FIG. 1) is preferably threaded on its distal end, and can thus serve as rod 34. Tool 30 thus allows the surgeon conveniently to apply tension to rod 34 and thence to insert 26 and graft ligament 15, while tubular member 32 restrains any tendency of the sleeve 24 to move. Tension in the graft ligament 15 can thus be adjusted conveniently after sleeve 24 and the distal tibial end of the graft ligament have been firmly and finally secured in their respective positions in the femur and tibia.

FIG. 4 shows a cross-sectional view of the sleeve 24 placed in the femoral bone tunnel 12a. As indicated, sleeve 24 comprises a number of radially-extended gripping members 24a for ensuring a good bond between the sleeve and bone tunnel 12a. In the preferred embodiment shown, gripping members 24a comprise a continuous thread, allowing sleeve 24 to be turned into a tapped portion 12c of bone tunnel 12a in femur 12.

An internal bore 24b formed in sleeve 24 is provided with circular ridges indicated generally at 24c; these are asymmetrical as shown in order to cooperate with mating asymmetrical circumferential ridges 26a formed on insert 26. As illustrated in FIG. 3, the ridges 24c and 26a cooperate such that the insert 26 can be pulled through the sleeve 24 only in one direction, i.e., leftwardly in FIG. 3. The sleeve 24 is molded of a somewhat resilient, bio-resorbable polymeric material such as poly-l-lactic acid (PLLA), so that it can be deformed radially outwardly sufficiently to allow the ridges 26a of the insert 26 to slide past ridges 24c of sleeve 24. The insert 26 may be molded of the same material.

In a preferred embodiment of the invention, circular ridges 24c and 26a were formed of frustoconical shape, as shown, with relatively sharp edges 24f and 26f respectively. In this embodiment, the angle of the frustoconical surfaces with respect to the axis of the bone tunnels is preferably about 73°. The minor diameter of the ridges of the insert is 0.150 inches, and their major diameter 0.190 inches, while the corresponding diameters of the ridges in the internal bore of the sleeve are 0.150 and 0.200 inches, respectively. As noted, some minor deformation of at least the sleeve takes place as the insert is pulled through the sleeve, and the relatively sharp edges 24f and 26f may also become somewhat rounded as the insert is pulled through the sleeve in use. In this embodiment, the minor outside diameter of the sleeve is at least 6.553 mm (0.258 inches), to provide sufficient wall strength. The major outside diameter of the sleeve may be 10 mm (0.394 inches); the diameter of the portion 12b of the femoral bone tunnel may be 10.5 mm, and the diameter of the smaller portion 12c 6 mm, before tapping to receive a threaded sleeve 24.

In the preferred embodiment tested, the sleeve and insert were each molded of PLLA to the dimensions given above. Use of other materials would likely call for some variation of these dimensions, as understood by those of skill in the art. Engagement of four mating ridges on the sleeve and insert resulted in an average pullout strength in excess of 115 lbs; that is, in tests performed holding the sleeve in a vise, an axial force of more than 115 lbs was required to pull the insert through the sleeve. While a greater number of ridges are preferably provided on one or both of the sleeve and insert, to ensure an adequate range of adjustment, at least a predetermined number (e.g., four) of the cooperating ridges formed on the sleeve and insert should be engaged with one another to provide adequate pullout strength.

As illustrated in FIGS. 4 and 5, the sleeve may also have radially extending surfaces 24d extending through its bore 24b so as to receive torque from a driver 40. In this case the internal ridges 24c are generally circular. Driver 40 is generally of screwdriver configuration, that is, having a gripping handle (not shown) and an elongated driver shaft of cross-sectional shape corresponding to the radially-extending surfaces 24d, as illustrated in FIG. 5, and a flange 40a for exerting axial force on sleeve 24. It will be observed that driver 40 is cannulated, that is, hollow, such that sleeve 24 and driver 40 can be assembled over guide wire 14, ensuring that sleeve 24 is properly received within bone tunnel 12a. Driver 40 can therefore be used to turn sleeve 24, threading it into tunnel 12a formed in femur 12.

The sleeve 24 may also have radially extending slots 24e formed in its distal end surface for receiving radially extending ears 36a formed on cannula 36; cannula 36 can be turned in order to exert torque on the sleeve 24 if needed to adjust its final position. This aspect of the invention is discussed further below.

As also shown in FIG. 3, insert 26 comprises circumferential ridges 26a as mentioned, and is fitted with means at either end for being attached to the graft ligament 15 and to tension member 34 so as to be pulled through sleeve 24. In the embodiments shown in FIG. 3 and in FIG. 7, the graft ligament is simply sutured to insert 26 (26' in FIG. 7) by means of an eyelet 26b provided for this purpose. In the embodiment of FIG. 3, the tension member 34 is a rod (which as mentioned may be guide pin 14), having a threaded distal end 34a for being received within a threaded recess 26c in the insert. In the embodiment shown in FIG. 7, the tension member is simply a suture 44 received within a second eyelet 26d provided for this purpose. Suture 44 may be received within an eyelet (not shown) formed in the distal end of guide wire 14, such that guide wire 14 is used to draw the graft ligament into position.

In the embodiment shown in FIG. 3, tension is applied to the tension rod 34 by tool 30. As noted above, the guide wire 14, placed initially to guide the formation of bone tunnels 10a and 12a, can be threaded so as also to serve as tension rod 34, or a separate tension rod may be provided.

As shown schematically in FIG. 3, tool 30 includes a hand grip 46 and a trigger 48. Trigger 48 is pivoted with respect to the handle 46 at a pivot point 50 and is provided with a spring-loaded pawl 52. One end of pawl 52 is received within notches 54 formed in an actuator 43, secured to tension rod 34 by a collet-type clamp indicated generally at 45, or similar means. See FIG. 8. Accordingly, when the surgeon pulls trigger 48 toward handle 46, tension member 34 is drawn inwardly through tubular member 32. Tubular member 32 bears against the proximal end surface of sleeve 24, either directly or through an intermediary cannula 36, as shown in FIG. 2, to ensure that sleeve 24 does not move axially as insert 26 is pulled therethrough to adjust the tension on graft ligament 15. In an alternative arrangement, actuator 43 could be replaced by a tubular sleeve for receiving tension member 34, and having circumferential grooves for receiving pawl 52; this tubular sleeve might typically be secured to tension member 34 (which again may be guide pin 14, or may be a separate member) by a collet-type clamp, generally as illustrated in FIG. 8.

It will be appreciated that because tool 30 both applies the tension to insert 26, by way of tension member 34, and restrains sleeve 24, by way of tubular member 32, substantial tension can be exerted in a carefully controlled fashion; this in turn allows insert 26 to be a relatively tight fit within sleeve 24, providing a very secure anchor.

In the preferred embodiment, the spacing of ridges 26a on insert 26 and 24c in sleeve 24 are such that each "click" felt or heard by the surgeon as the insert moves with respect to the sleeve corresponds to a 2 mm extension of the graft ligament. It has been found in experimental work that this allows excellent control of the tension applied to the ligament 15.

Completing discussion of the anchor assembly of the invention, FIG. 7 also shows an alternative version of sleeve 24, numbered 24' in this view, wherein the gripping means are typically provided as circumferentially extending ridges 24a'. Numerous alternative gripping means for ensuring the insert is securely received within the bone tunnel 12a are also within the skill of the art, including radially-extending barbs. In this case, sleeve 24 is simply pushed into its final position within a bone tunnel and need not be turned to be threaded thereinto. The internal structure of sleeve 24' is essentially as described above with respect to sleeve 24 and coacts in an identical way with ridges 26a formed on either of the insert designs shown.

It will therefore be appreciated that according to the invention, a ligament may be anchored at one or both ends by first disposing a sleeve 24 in a bone tunnel, thereafter inserting an insert having had a graft ligament secured thereto, and pulling the insert through the sleeve 24 until a desired relative position has been achieved.

The method of ligament replacement according to the invention therefore comprises the steps of forming the bone tunnels, disposing the sleeve according to the invention in a bone tunnel formed in a first bone, fabricating a graft ligament and securing one end to an insert according to the invention, fixing the opposite end of the ligament, e.g., using an interference screw 22 as shown in FIG. 2, or by placing a second sleeve 24 and using a second insert 26 secured to the opposite end of graft 15, and then pulling the insert(s) through the sleeve(s) until the desired degree of tension has been achieved.

While it is within the scope of the invention to employ the anchor assemblies according to the invention at both ends of the graft ligament, as indicated, typically the additional degree of tension adjustment thus provided will not be necessary, as the surgeon will be able to judge the tension to be applied fairly accurately when first making the assembly. According to a more typical procedure, the surgeon will pull the insert partway into the sleeve before affixing the opposite end of the graft ligament to the other bone, e.g., using an interference screw to secure the opposite bone plug 20 to the tibia, as shown in FIG. 2, followed by pulling the insert a few more millimeters into the sleeve for final tension adjustment. In this way the surgeon can be ensured that the insert is substantially fully received in the sleeve when the procedure is complete.

As noted, the final tension adjustment can be made using tool 30 to simply pull the insert 26 a few more millimeters into sleeve 24. The tension member is then disengaged and removed, the wounds closed and the bone allowed to grow around the sleeve and bone plugs, firmly securing the graft ligament in place.

FIG. 9 shows a combined cannula and trocar tool 60 useful in practice of the invention, and illustrates additional refinements in the method of the invention. Specifically, tool 60 comprises a cannulated trocar portion 62, that is, an elongated tubular member having a cutting point or drill tip 64 for cutting bone tunnels 10a and 12a, and a cannula portion 36'. Cannula portion 36' is essentially similar to the cannula 36 discussed above, but has an internally-threaded bore for receiving a threaded end 66 of trocar portion 62.

In use, after guide wire 14 has been placed, trocar portion 62 and cannula portion 36' are assembled, and trocar portion 62 used to cut bone tunnels 10a and 12a. After the trocar portion exits the skin, it is removed from cannula portion 36'. Cannula portion 36' remains in place, so as to avoid unnecessary disturbance caused by its removal and replacement. If the tibial bone tunnel and a portion of the femoral bone tunnel are to be of larger diameter than that of trocar portion 62, the larger-diameter bone tunnels will normally be formed, e.g., using a tubular reamer fitting over guide wire 14, before the trocar/cannula assembly 60 is used to complete the femoral bone tunnel. After removal of the trocar portion 62, cannula portion 36' can then be used as described above, to prevent motion of sleeve 24 as force is exerted thereon by pulling insert 26 therethrough. Cannula portion 36' is also provided with ears 36a, for exerting torque on sleeve 24, as may be necessary to remove or relocate sleeve 24.

If this combined tool 60 is to be used for placement of a sleeve 24 conforming to the embodiment discussed in detail above, a tubular reamer of 10.5 mm diameter is passed over the guide wire 14, and used to form the entire length of the tibial tunnel and a portion 12b of the femoral tunnel of depth 5–10 mm greater than the length of the femoral bone block 18. This reamer is then removed, and a trocar/cannula assembly 6 mm in diameter used to complete the femoral tunnel. It is also within the scope of the invention to form the entire length of both tunnels using the trocar/cannula assembly, remove the trocar, and use a reamer to enlarge the tibial tunnel and a portion of the femoral tunnel, as desired.

While several preferred embodiments of the invention have been disclosed in detail, it will be appreciated by those of skill in the art that numerous additional modifications and improvements can be made thereto without departure from the spirit and scope of the invention, which is therefore to be limited only by the appended claims.

What is claimed is:

1. An anchor assembly for securing one end of an elongated ligament graft in a tunnel drilled in bone, comprising a generally tubular elongated sleeve and a mating elongated insert, said generally tubular elongated sleeve having gripping means on an outer surface thereof for being secured within said tunnel, and a bore extending therethrough for receiving said mating insert, said mating insert comprising means at a first end thereof for being secured to said ligament graft, and means at an opposite end thereof for being releasably connected to a tension member for pulling said insert through said bore in said sleeve in a first direction to reach a desired position therealong, and the bore in said sleeve member and the outer surface of said insert comprising cooperating members, said cooperating members being shaped such that said insert can be pulled through said sleeve only in said first direction, whereby said insert is restrained by said sleeve from moving in a direction opposite to said first direction responsive to tension exerted on said insert in the opposite direction by said ligament graft.

2. The anchor assembly of claim 1, wherein said gripping means on an outer surface of said sleeve comprise radially-extending barb members around said sleeve.

3. The anchor assembly of claim 1, wherein said gripping means on an outer surface of said sleeve define an external thread, whereby said sleeve may be threaded in a tunnel drilled in bone.

4. The anchor assembly of claim 3, wherein the internal bore of said sleeve is formed to comprise radially-extending surfaces extending along at least a portion of said bore, in addition to said cooperating members, for receiving torque from a correspondingly-shaped tool in order to thread said sleeve into said tunnel.

5. The anchor assembly of claim 1, wherein said cooperating members comprise a series of generally circular ridges formed on each of the bore in said sleeve and on the outer surface of said insert, said ridges being formed asymmetrically with respect to the direction of elongation of the sleeve and insert, whereby said insert can be pulled along the bore in one direction, but is prevented from moving in the opposite direction therealong.

6. The anchor assembly of claim 5, wherein said series of generally circular ridges are each generally frustoconical.

7. The anchor assembly of claim 5, wherein said sleeve is formed of a resilient plastic material, and said insert is a solid cylindrical member in the portion thereof over which said ridges are formed, whereby said sleeve is deformed radially outwardly as said said ridges on said insert move past said cooperating ridges in the bore of said sleeve, as said insert is pulled along said sleeve.

8. The anchor assembly of claim 7, wherein said sleeve is molded of a bioresorbable plastic material.

9. The anchor assembly of claim 8, wherein said insert is also molded of a bioresorbable plastic material.

10. The anchor assembly of claim 1, wherein said means at an end of said insert for being releasably connected to a tension member comprises an eyelet for receiving a suture for pulling said insert through said sleeve.

11. The anchor assembly of claim 1, wherein said means at an end of said insert for being releasably connected to a tension member comprises a threaded bore for receiving a cooperatively-threaded tension member.

12. The anchor assembly of claim 1 and means for restraining axial motion of said sleeve while tension is applied to said insert to pull said insert through said sleeve in said first direction.

13. The anchor assembly of claim 12, wherein said means for applying tension to said insert while restraining axial motion of said sleeve comprises a tension member for applying tension to said insert, a tubular member for having a distal end thereof braced with respect to said sleeve, said tubular member receiving said tension member, and means for applying tension to said tension member with respect to said tubular member.

14. The anchor assembly of claim 13, further comprising a cannula fitting over said tension member and abutting said sleeve and said tubular member.

15. The anchor assembly of claim 1, and a cannula adapted to abut said sleeve for restraining axial motion thereof as force is applied to said insert to pull said insert through said sleeve.

16. The anchor assembly of claim 15, wherein said cannula is further adapted to mate with and transmit torque to said sleeve.

17. The anchor assembly combination of claim 15, wherein said cannula is further adapted to be threadedly joined to a trocar for forming said bone tunnels.

18. A method for securing one end of a ligament graft in a bone tunnel, comprising the steps of:
providing a generally tubular elongated sleeve having gripping means on an outer surface thereof and a bore extending therethrough for receiving a mating insert,
securing said sleeve within said tunnel,
providing a mating insert, the bore in said sleeve member and the outer surface of said insert comprising cooperating members, said cooperating members being shaped such that said insert can be pulled through said sleeve only in a first direction,
securing a first end of said insert to one end of a ligament graft,
releasably securing a tension member to an opposite end of said insert, and
exerting tension on said tension member in order to pull said insert through said bore in said sleeve in said first direction, while simultaneously pulling said graft through said tunnel in order to reach a desired position therealong.

19. The method of claim 18, wherein said gripping means on an outer surface of said sleeve comprise radially-extending barb members.

20. The method of claim 18, wherein said gripping means on an outer surface of said sleeve define a thread, and said method comprises the further step of turning said sleeve such that it is threaded into said tunnel.

21. The method of claim 20, wherein the internal bore of said sleeve is formed to comprise radially-extending surfaces extending along at least a portion of said bore, in addition to said cooperating members, for receiving torque from a correspondingly-shaped tool in order to turn said sleeve and thread it into said tunnel.

22. The method of claim 18, wherein said cooperating members comprise a series of generally circular ridges formed on each of the bore in said sleeve and on the outer surface of said insert, said ridges being formed asymmetrically with respect to the direction of elongation of the sleeve and insert, whereby said insert can be pulled along the bore in one direction, but is prevented from moving in the opposite direction therealong.

23. The method of claim 22, wherein said ridges are generally frustoconical.

24. The method of claim 22, wherein said sleeve is formed of a resilient material, and said insert is a solid cylindrical member in the portion thereof over which said ridges are formed, whereby said sleeve is deformed radially outwardly as said ridges on said insert move past said cooperating ridges in the bore of said sleeve, as said insert is pulled along said sleeve.

25. The method of claim 18, wherein said tension member comprises a suture passing through an eyelet in said insert.

26. The method of claim 18, wherein said tension member is a threaded rod releasably secured to an end of said insert by being threaded into a bore thereof.

27. The method of claim 18, wherein tension is applied to said insert to pull said insert through the bore in said sleeve using a tool comprising a tubular member having a distal end effectively abutting said sleeve, said tool further comprising a tension member movable with respect to said tubular member for applying tension to said insert.

28. The method of claim 18, comprising the further step of securing a second end of the ligament graft at a predetermined site, and adjusting the tension of said ligament graft after said second end thereof has been secured by applying further tension to said tension member, pulling said insert further into said sleeve.

29. A method of securing a ligament graft to opposed bones of a body joint, comprising the steps of:
forming bone tunnels in said opposed bones;
providing a generally tubular elongated sleeve having gripping means formed on an outer surface thereof and a bore extending therethrough for receiving a mating insert,
securing said sleeve within a first of said tunnels,
providing a mating insert, the bore in said sleeve member and the outer surface of said insert comprising cooperating members, said cooperating members being shaped such that said insert can be pulled through said sleeve only in a first direction,
securing a first end of said insert to a first end of a ligament graft,
releasably securing a tension member to an opposite end of said insert,
passing said tension member into a distal end of and through the second of said tunnels, into the first of said tunnels and through said sleeve therein, and out through a proximal end of said first tunnel, exerting tension on said tension member in order to pull said insert and said ligament graft in said first direction through the second of said tunnels, and to pull said insert into said bore in said sleeve through said tunnel in order to reach a desired position therealong, securing a second end of said ligament graft within said second tunnel, and detaching said tension member from said insert.

30. The method of claim 29, comprising the further step of adjusting the tension of said ligament graft after said second end thereof has been secured by applying further tension to said tension member, pulling said insert further into said sleeve.

31. The method of claim 29, wherein said tension member is a threaded rod releasably secured to an end of said insert by being threaded into a bore thereof.

32. The method of claim 29, wherein tension is applied to said rod to pull said insert further into said sleeve using a tool comprising a tubular member having a distal end effectively abutting said sleeve, means disposed coaxially within said tubular member for applying tension to said insert, and means for pulling said means for applying tension through said tubular member.

33. The method of claim 29, wherein said gripping means on an outer surface of said insert comprise a thread, and said method comprises the further step of threading said insert into said tunnel by application of torque to said insert.

34. The method of claim 33, wherein the internal bore of said sleeve is formed to comprise radially-extending surfaces extending along at least a portion of said bore, in addition to said cooperating members, for receiving torque from a correspondingly-shaped tool in order to turn said sleeve and thread it into said tunnel.

35. The method of claim 29, wherein said cooperating members comprise a series of generally circular ridges formed on each of the bore in said sleeve and on the outer surface of said insert, said ridges being formed asymmetrically with respect to the direction of elongation of the sleeve and insert, whereby said insert can be pulled along the bore in one direction, but is prevented from moving in the opposite direction therealong.

36. The method of claim 31, wherein said sleeve is formed of a resilient plastic material, and said insert is a solid cylindrical member in the portion thereof over which said ridges are formed, whereby said sleeve is deformed radially outwardly as said said ridges on said insert move past said cooperating ridges in the bore of said sleeve, as said insert is pulled along said sleeve.

37. The method of claim 29, wherein said bone tunnels are formed using a trocar threadedly connected to a cannula, and comprising the further step of removing said trocar from said cannula after formation of said bone tunnels, such that said cannula may be employed to prevent motion of said sleeve along said tunnels as tension is applied to said insert to pull said insert through said sleeve.

38. The method of claim 29, wherein said step of forming bone tunnels in said opposed bones comprises the step of passing an elongated guide pin through said opposed bones, said pin having a pointed tip at one end and means for being releasably secured to said insert at its opposite end, whereby said guide pin serves as said tension member for pulling said insert into said sleeve.

39. The method of claim 38, wherein said means at the opposite end of guide pin for being releasably secured to said insert comprises a thread for being received within a threaded aperture at one end of said insert.

40. A method of securing a ligament graft to opposed bones of a body joint, comprising the steps of:

passing a guide pin having a proximal end and a distal end through both of said bones, such that the distal end thereof extends out through skin over a first side of said joint, while its proximal end remains accessible on the other side of said joint;

drilling a first bone tunnel in one of said bones by passing a cannulated bone removing device along said guide pin from said proximal end and through said one of said bones, said cannulated bone removing device being of a first predetermined diameter;

drilling a second bone tunnel into the other of said bones by passing said cannulated bone removing device further along said guide pin and partially into the other of said bones;

providing a cannulated trocar/cannula assembly having a distal trocar end and a proximal cannula end, said ends being axially aligned and separably joined together, said trocar/cannula assembly having a diameter less than said predetermined diameter;

placing said trocar/cannula assembly over said proximal end of said guide pin and passing said assembly through the bone at the end of said second bone tunnel and through the skin;

disengaging said trocar end from said cannula end and leaving said cannula end in said bone and extending through said skin;

providing a generally tubular elongated sleeve having gripping means formed on an outer surface thereof and a bore extending therethrough for receiving a mating insert;

employing a cannulated driver to drive said sleeve along said guide pin into the bone at the distal end of said second bone tunnel;

removing said driver;

providing a mating insert, the bore in said sleeve member and the outer surface of said insert comprising cooperating members, said cooperating members being shaped such that said insert can be pulled through said sleeve only in a first direction;

securing a first end of said insert to a first end of a ligament graft;

releasably securing the distal end of said guide pin to an opposite end of said insert;

exerting tension on said guide pin in said first direction while exerting pressure on said sleeve in the opposing direction in order to pull said insert into said sleeve and said graft into said bone while preventing motion of said sleeve; and detaching said guide pin from said insert.

* * * * *